(12) United States Patent
Dempster et al.

(10) Patent No.: US 6,702,764 B2
(45) Date of Patent: Mar. 9, 2004

(54) APPARATUS AND METHODS FOR PLETHYSMOGRAPHIC MEASUREMENT OF INFANT BODY COMPOSITION

(75) Inventors: Philip T. Dempster, Concord, CA (US); Mark Lowe, Danville, CA (US)

(73) Assignee: Life Measurement, Inc., Concord, CA (US)

( * ) Notice: Subject to any disclaimer, the term of this patent is extended or adjusted under 35 U.S.C. 154(b) by 209 days.

(21) Appl. No.: 10/036,139

(22) Filed: Dec. 31, 2001

(65) Prior Publication Data
US 2003/0125643 A1 Jul. 3, 2003

(51) Int. Cl.[7] .......................... A61B 5/103; A61B 5/117

(52) U.S. Cl. ..................................................... 600/587

(58) Field of Search .............................. 600/587, 300, 600/529, 560; 73/149, 1.66, 1.68, 433; 119/420; 128/200.14, 203.12

(56) References Cited

U.S. PATENT DOCUMENTS

| | | |
|---|---|---|
| 4,184,371 A | 1/1980 | Brachet |
| 4,369,652 A | 1/1983 | Gundlach |
| 4,406,289 A | 9/1983 | Wesseling et al. |
| 4,539,997 A | 9/1985 | Wesseling et al. |
| 4,640,130 A | 2/1987 | Sheng et al. |
| 4,676,253 A | 6/1987 | Newman et al. |
| 4,841,982 A | 6/1989 | Nikiforov et al. |
| 4,888,718 A | 12/1989 | Furuse |
| 4,972,842 A | 11/1990 | Korten et al. |
| 5,105,825 A | 4/1992 | Dempster |
| 5,379,777 A | 1/1995 | Lomask |
| 5,450,750 A | 9/1995 | Abler |
| 5,620,005 A | 4/1997 | Ganshorn |

OTHER PUBLICATIONS

Bailey et al., "Test–Retest Reliability of Body Fat Percentage Results Using Dual Energy X–Ray Absorptiometry and the BOD POD," *Presented at the American College of Sports Medicine 48th Annual Meeting*, May 30–Jun. 2, 2001 in Baltimore, Maryland (abstract only).

Biaggi et al., "Comparison of Air–Displacement Plethysmography with Hydrostatic Weighing and Bioelectrical Impedance Analysis for the Assesment of Body Composition in Healthy Adults 1–3," *American Journal of Clinical Nutrition* vol. 69: pp. 898–903 (1999).

Dempster et al., "A New Air Displacement Method for the Determination of Human Body Composition," *Med Sci Sports Exerc*. Dec. 1995; 27(12): 1692–7.

Dewit et al., "Whole Body Air Displacement Plethysmography Compa5red with Hydrodensitometry for Body Composition Analysys," *Archives of Disease in Childhood* vol. 82 No. 2: pp. 159–164 (Feb. 2000).

Ellis et al., "Can Air–Displacement Plethysmography Replace Hydrodensitometry for Body Composition Analysis in Children and Adults," *Presented at Experimental Biology 2001* in Orlando, Florida (abstract only).

(List continued on next page.)

*Primary Examiner*—Max F. Hindenburg
*Assistant Examiner*—Brian Szmal
(74) *Attorney, Agent, or Firm*—Fish & Neave; Mark D. Rowland

(57) ABSTRACT

Apparatus and methods relating to plethysmographic measurement of infant body composition are provided. A tray for receiving the infant subject to be measured is coupled to a sliding mechanism that slides the tray in and out of a plethysmographic measurement chamber, thereby reducing the footprint of said chamber and facilitating infant comfort during measurement. Further, an integrated weighing function is provided that determines the infant's weight while conducting body composition measurements.

33 Claims, 3 Drawing Sheets

OTHER PUBLICATIONS

Fields et al., "Body Composition Techniques and the Four–Compartment Model in Children," *Journal of Applied Physiology* vol. 89: pp. 613–620 (2000).

Gundlach et al., "The Plethysmometric Measurement of Total Body Volume," *Human Biology* vol. 58 No. 5: pp. 783–799 (oct. 1986).

Higgins et al., "Effect of Scalp and Facial Hair on Air Displacement Plethysmography Estimates of Percentage Body Fat," *Obes Res* 2001 May; 9(5): 326–330.

http://academic.wsc.edu/hpls/glass_s/onlineped103/chapter4.htm, "What Fat is Linked to; Slides 4, 13, 17, 20, 21, 23, 26, 28, 30" (Dec. 26, 2001).

http://www.geocities.com/HotSprings/5484/thesis/thesis2.htm, "Chapter II: Review of Literature on Body Composition" (Dec. 26, 2001).

http://hnrc.tufts.edu, "Laboratories and Programs: Body Composition Research Program" (Dec. 26, 2001).

http://www.nal.usda.gov/ttic/tektran/data/000009/27/0000092775.html, "Tektran Agriculture Research Service: Body Composition in Children and Adults by Air Displacement Plethysmography" (Dec. 26, 2001).

http://www.coe.uh.edu./~bsekula/pep6301/Ch.%2027%20Mkk.htm, "Body Composition Assessment" (Dec. 26, 2001).

http://odp.od.nih.gov/consensus/ta/015/015 intro.htm, "State of the Science Statements NIH Concensus Development Program: Bioelectrical Impedance Analysis in Body Composition Measurement—Dec. 12–14, 1994: 15. Bioelectrical Impedance Analysis in Body Composition Measurement" (Dec. 26, 2001).

http://brc.montana.edu/olympics/physiology/pb03.html, "Physiology & Psychology Performance Benchmarks: Body Composition and Body Mass" (Dec. 26, 2001).

LeCheminant et al., "Differences in Body Fat Percentage Measured Using Dual Energy X–Ray Absorptiometry and BOD POD in 100 Women," Presented at the *American College of Sports Medicine 48th Annual Meeting*, May 30–Jun. 2, 2001 in Baltimore, Maryland (abstract only).

Lockner et al, "Comparison of Air–Displacement Plethysmography, Hydrodensitometry, and Dual X–ray Absorptiometry for Assessing Body Composition of Children 10 to 18 Years of Age," *Annals of the New York Academy of Sciences* vol. 904—*In Vivo Body Composition Studies*: pp. 72–78 (May 2000).

Manddalozzo et al., "Concurrent Validity of the BOD POD and Dual Energy X–Ray Absorptiometry Techniques for Assessing the Body Fat Percentage in Young Women," Presented at the *American College of Sports Medicine 48th Annual Meeting*, May 30–Jun. 2, 2001 in Baltimore, Maryland (abstract only).

McCrory et al., "Evaluation of a New Air Displacement Plethysmograph for Measuring Human Body Composition," *Med Sci Sports Exerc*. Dec. 1995; 27(12): 1686–91.

McCrory et al., "Comparison of Methods for Measuring Body Composition Responses to Progressive Resistance Training in Hispanic Elders with Type 2 Diabetes," Presented at *Experimental Biology* 2001 in Orlando, Florida (abstract only).

Miyatake et al., "A New Air Displacement Plethysmograph for the Determination of Japanese Body Composition," *Diabetes Obes Metab* Nov. 1999; 1(6): 347–51.

Nicholson et al., "Estimation of Body Fatness by Air Displacement Plethysmography in African American and White Children," *Pediatric Research* vol. 50 No. 4: pp. 467–473 (2001).

Nunez et al., "Body Composition in Children and Adults by Air Displacement Plethysmography," *Eur J Clin Nutr.* May 1999; 53(5): 382–7.

Wagner et al., "Techniques of Body Composition Assessment: A Review of Laboratory and Field Methods," *Research Quarterly for Exercise and Sport:* pp. 135–149 (Jun. 1999).

Yee et al., "Calibration and Validation of an Air–Displacement Plethysmography Method for Estimating Percentage Body Fat in an Elderly Population: A Comparison among Compartmental Models 1–3," *American Journal of Clinical Nutrition* vol. 74: pp. 637–642 (2001).

APPARATUS AND METHODS FOR PLETHYSMOGRAPHIC MEASUREMENT OF INFANT BODY COMPOSITION

FIELD OF THE INVENTION

This invention relates generally to plethysmographic measurement of human body composition. More specifically, the present inventions relate to apparatus and methods for plethysmographic measurement of body composition for infant subjects.

BACKGROUND OF THE INVENTION

The assessment of body composition, including measurement of fat and fat-free mass, provides physicians with important information regarding physical status. Excess body fat has been associated with a variety of disease processes, such as cardiovascular disease, diabetes, hypertension, hyperlipidemia, kidney disease, and musculoskeletal disorders. Low levels of fat free mass have been found to be critically adverse to the health of certain at-risk populations, such as infants and the elderly.

Similarly, particularly with respect to infants, body weight has been shown to be useful as a diagnostic measurement for the assessment of physical status. Disturbances in health and growth, regardless of origin, almost always affect body weight in newborns and infants. In particular, for very low birth weight infants, weight and weight gain patterns are relevant both in determining infant energy needs and in evaluation of health progression and physical development.

A variety of methods are currently used in the assessment of body composition. One common method is a skin fold measurement, typically performed using calipers that compress the skin at certain points on the body. While non-invasive, this method suffers from poor accuracy on account of variations in fat patterning, misapplication of population specific prediction equations, improper site identification for compressing the skin, poor fold grasping, and the necessity for significant technician training to administer the test properly. Moreover, no successful methodology for determining infant body composition using skinfold measurement has been devised.

Another method employed is bioelectric impedance analysis ("BIA"). Bioelectric impedance measurements rely on the fact that the body contains intracellular and extracellular fluids that conduct electricity by passing a high frequency electric current through the body, BIA determines body composition based on the bodies' measured impedance in passing current and known impedance values for human muscle tissue. However, this method can be greatly affected by the state of hydration of the subject, and variations in temperature of both the subject and the surrounding environment. Moreover, BIA has not been successfully applied with infant subjects.

The most common method used when precision body composition measurements are required is hydrostatic weighing. This method is based upon the application of Archimedes principle, and requires weighing the subject on land, repeated weighing under water, and an estimation of air present in the lungs of the subject using gas dilution techniques. However, hydrodensitometry is time consuming, typically unpleasant for the subjects, requires both significant subject participation and considerable technician training and, due to the necessary facilities for implementation, is unsuitable for clinical practice. Further, the application of hydrodensitometry to infant populations is precluded by the above concerns.

One technique offering particular promise is performing body mass measurement is the use of plethysmography. Plethysmographic methods determine body composition through application of Boyle's law to the differentiation in volume between the volume of an empty measurement chamber, and the volume of the chamber with the subject to be measured inside. Examples of this technique are disclosed in U.S. Pat. No. 4,369,652 issued to Gundlach, U.S. Pat. No. 5,450,750 issued to Adler, U.S. Pat. No. 4,184,371 issued to Brachet, and U.S. Pat. No. 5,105,825, issued to Dempster. This procedure, in contrast to hydrodensitometry, does not cause anxiety or discomfort in the subject, and due to the ease and non-invasiveness of the technique, can in theory be applied to infant subjects for whom hydrodensitometry is impractical.

However, conducting plethysmographic body measurement of infants using current plethysmographic chambers has proven to be impractical. Current plethysmographic chambers are not sized for infants. Given the lower body mass measurements of infant subjects, even more precise determination of chamber volume is required than for adults if such present chambers were to be used. Further, present chambers require the subject to be measured to remain in a seated position within the chamber during measurement, which is not feasible for use with infant subjects.

In view of the foregoing, it would be desirable to provide a plethysmographic chamber for measurement of infant body composition.

It would further be desirable to provide a system which integrates other useful diagnostic measurements, such as determination of body weight, in a plethysmographic measurement chamber for infants.

SUMMARY OF THE INVENTION

In view of the foregoing, it is an object of the present invention to provide a plethysmographic chamber for measurement of infant body composition.

It is another object of the present invention to provide a system which integrates other useful diagnostic measurements, such as determination of body weight, in a plethysmographic measurement chamber for infants.

BRIEF DESCRIPTION OF THE DRAWINGS

The foregoing and other objects of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1:
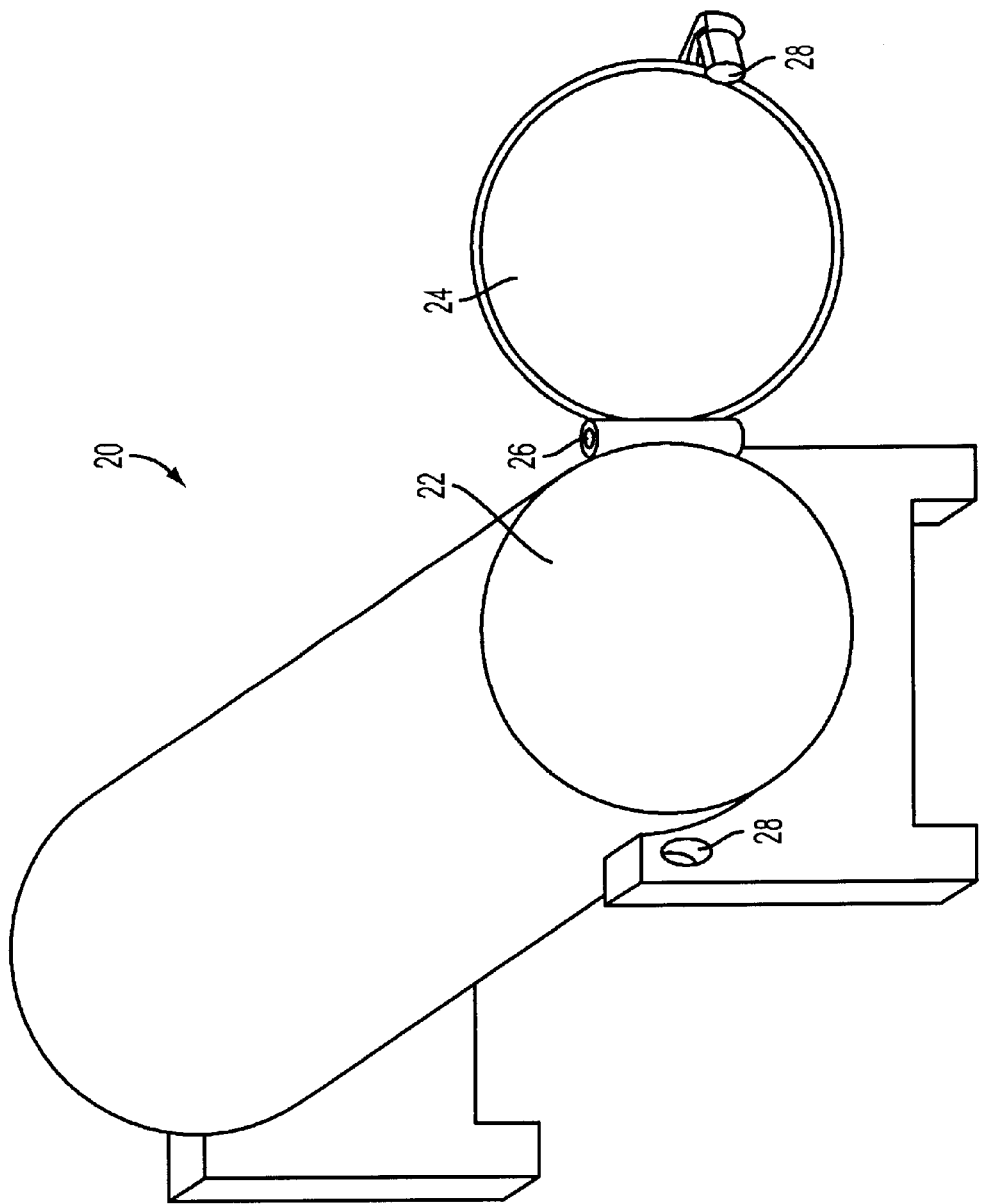
FIG. 1 is a representation of the infant sized plethysmographic chamber of the present invention.

Referring to FIG. 1, a representational view of the infant sized plethysmographic chamber is shown. Plethysmographic chamber 20 includes chamber opening 22, chamber door assembly 24, hinge 26, and latch 28. Door assembly 24 pivots about hinge 26, allowing for entry of the infant subject into the chamber, and closure of chamber door assembly 24. Methods and apparatus for providing repeatable door closure for infant plethysmographic chambers are described in co-pending U.S. patent application Ser. No. 10/036,352, entitled Apparatus and Methods For Repeatable Door Closure in a Plethysmographic Measurement Chamber, applied for by Philip Dempster and Mark Lowe, and filed on even date herewith, which application is hereby incorporated by reference in its entirety.

Figure 2:
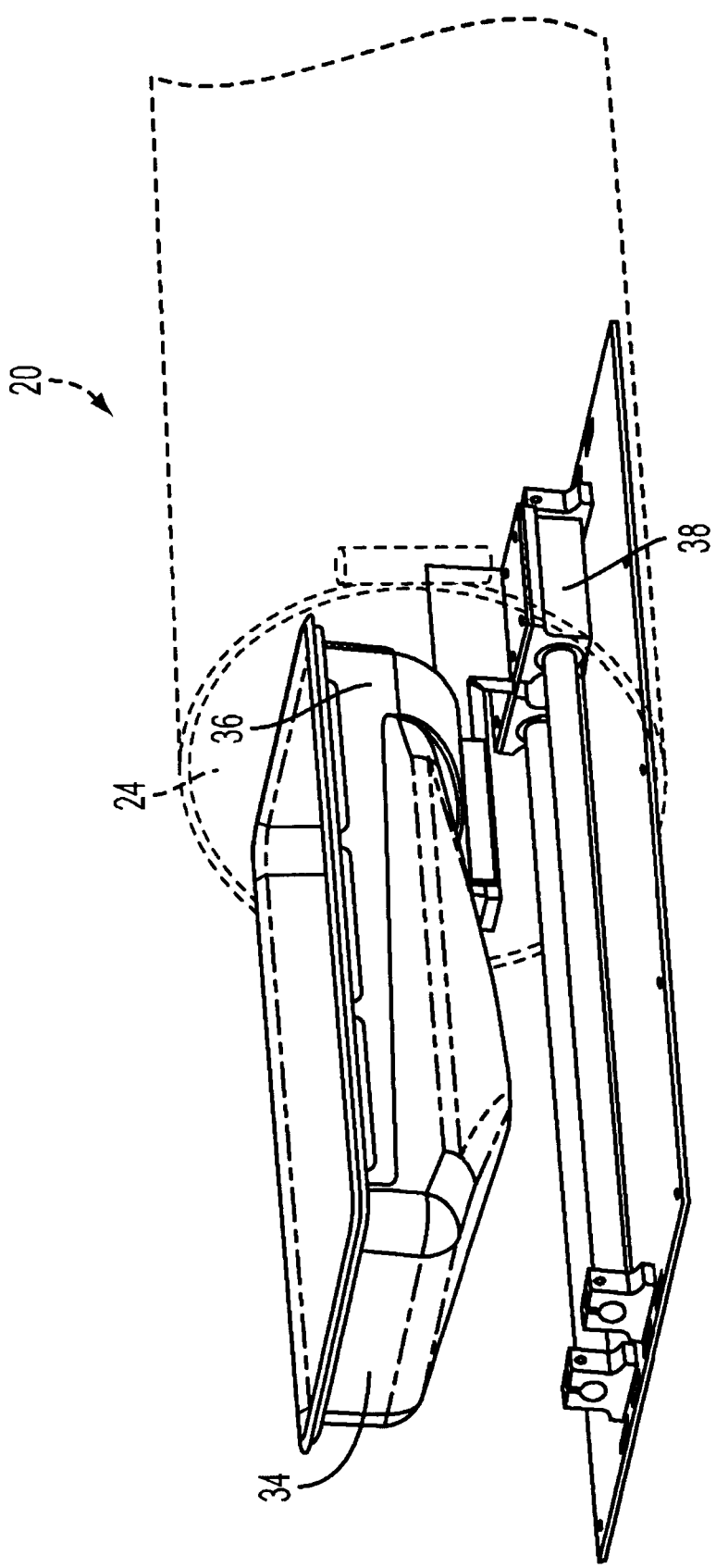
FIG. 2 is a detailed view of the slide and tray arrangement of the present invention.

Referring now to FIG. 2, a detailed view of the sliding tray assembly of the present invention is described. Infant subject 30 is laid in tray 34, which is supported by tray carriage 36. In a preferred embodiment, tray carriage 36 is a metal support frame for tray 34. Alternatively, tray carriage 36 can be any support structure for tray 34. Tray 34 allows the infant to be placed in a comfortable position in the plethysmographic chamber during measurement of the infant's body composition.

Tray carriage 36 enters chamber 20 by means of a sliding mechanism 38. By placing the infant in the prone position in tray 34, and providing for a sliding mechanism for insertion and removal of tray 34 from chamber 20, the footprint of chamber opening 22 is minimized. By minimizing the footprint of chamber opening 22, a smaller door assembly can be used, resulting in less stress in the plane of closure for door assembly 24, and more repeatable chamber door closure.

In the preferred embodiment, sliding mechanism 38 is comprised of a pair of slide bearings mounted on a pair of slide rails. However, as one of ordinary skill in the art would recognize, alternative sliding mechanisms can be used in accord with the present invention. For example, wheels mounted to tray carriage 36, or rollers on an inner surface of chamber 20 could easily be used in place of slide bearings and rails.

Figure 3:
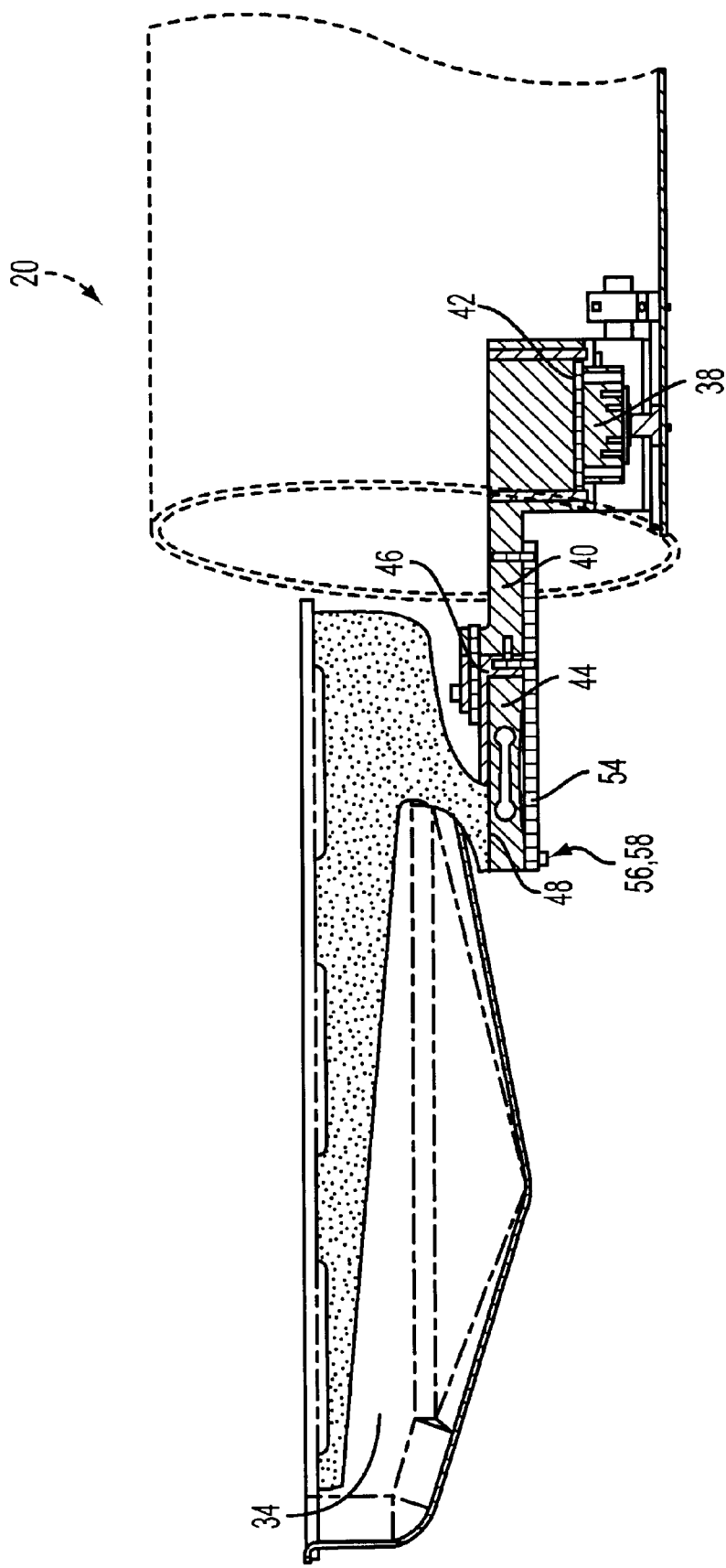
FIG. 3 is a detailed view of the integrated weighing function of the present invention.

Referring now to FIG. 3, a detailed view of the integrated weighing function for plethysmographic chamber 20 is described. Cantilevered arm 40 is coupled to measurement chamber 20 at arm base 42. Load cell 44 is suspended from cantilevered arm extension 46. Tray carriage 36 is fastened to load cell measurement plate 48 at the end of the load cell distal from cantilevered arm 40. Load cell 44 determines the weight of the infant subject based on the pressure exerted by tray carriage 36.

In a preferred embodiment, cantilevered arm 40 is mounted directly onto sliding mechanism 38, providing for more accurate weight measurement on account of the constant contact of tray 34.

Preferably, also mounted to cantilevered arm 40 is load cell overload protector arm 54. Load cell overload protector arm 54 is located underneath the load cell 44. At the distal end of load cell overload, protector arm 54 are load cell overload adjuster screws 56 and 58. Should the pressure presented at measurement point 50 cause too great deformation in load cell 44, thereby overloading the load cell, load cell overload adjuster screws 56 and 58 make contact with the underside of load cell 44, thereby providing support for and preventing damage to load cell 44 on account of the excess load.

One of ordinary skill in the art would recognize that alternative methods of determining weight of the infant subject other than the use of a load cell mounted to a cantilevered arm could also be used in accord with the present invention. For example, a load sensor affixed directly to chamber carriage 36 as opposed to mounted to a cantilevered arm. Alternatively, a scale located within chamber 20 could be used. Other alternatives include a capacitive transducer, or a force balance, both of which could be used in place of the load cell described above.

Further, while preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A plethysmographic chamber for measurement of infant body composition, the chamber comprising:
    a chamber wall, including an outer and an inner chamber surface;
    a chamber door assembly for allowing ingress and egress to said chamber;
    a tray for placement of a subject to be measured; and
    a sliding mechanism that moves said tray in and out of said chamber.

2. The chamber of claim 1, wherein said tray allows the subject to lie in a prone position.

3. The chamber of claim 1, wherein said tray is composed of a plastic compound.

4. The chamber of claim 1, further comprising:
    a tray carriage for suspending said tray above said inner chamber surface.

5. The chamber of claim 4, wherein the tray carriage is a metal frame surrounding said tray.

6. The chamber of claim 4, wherein said tray carriage is mounted to the sliding mechanism.

7. The chamber of claim 1, wherein the sliding mechanism comprises:
    one or more slide bearings mounted about one or more accompanying slide rails.

8. The chamber of claim 4, wherein the sliding mechanism comprises a set of wheels affixed to said tray carriage.

9. The chamber of claim 1, wherein the sliding mechanism comprises a set of rollers affixed to said inner chamber surface.

10. The chamber of claim 1, wherein the sliding mechanism comprises a slide affixed between a pair of guide rails.

11. The chamber of claim 1, wherein the chamber is cylindrical.

12. The chamber of claim 1, further comprising:
    a cantilevered arm; and
    a load cell mounted to said cantilevered arm;
    wherein the load cell provides for measurement of said subject's weight.

13. The chamber of claim 12, wherein the cantilevered arm is mounted to the sliding mechanism.

14. The chamber of claim 12, wherein the load cell determines said subject's weight by determining the pressure applied to said tray by said subject.

15. The chamber of claim 14, wherein the load cell is directly coupled to said tray.

16. The chamber of claim 12, further comprising:
    a tray carriage for suspending said tray above said inner chamber surface.

17. The chamber of claim 16, wherein the load cell is directly coupled to said tray carriage.

18. The chamber of claim 12, further comprising:
    an overload protector arm mounted to said cantilevered arm, wherein said overload protector arm prevents said load cell from over-deformation.

19. The chamber of claim 18, wherein the overload protector arm further comprises:
    one or more adjustable spacers extending from the surface of said overload protector arm, wherein said spacers define a maximum deformation distance of said load cell.

20. The chamber of claim 1, further comprising means for weighing said subject while said subject is in said load tray.

21. The chamber of claim 20, wherein the means for weighing said subject is a load cell.

22. The chamber of claim 20, wherein the means for weighing said subject is a force balance.

23. The chamber of claim 20, wherein the means for weighing said subject is a capacitive transducer.

24. An assembly for weighing an infant subject in a plethysmographic chamber, the assembly comprising:

a support structure coupled to an inner surface of said plethysmographic chamber; and a load cell mounted to said support structure.

25. The assembly of claim 24, wherein the support structure further comprises a cantilevered arm.

26. The assembly of claim 24, further comprising an overload protector arm for preventing over-deformation of the load cell.

27. The assembly of claim 26, further comprising:

one or more spacers mounted to said overload protector arm, wherein said spacers determine the maximum deformation of said load cell.

28. The assembly of claim 27, wherein said one or more spacers are adjustable.

29. The assembly of claim 27, wherein said overload protector arm is mounted to said support structure.

30. The assembly of claim 22, wherein the support structure is coupled to the inner surface of said chamber by a sliding mechanism for sliding the subject in and out of said chamber.

31. A method for performing diagnostic measurements on an infant subject, the method comprising:

placing the subject in a plethysmographic measurement chamber;

weighing the subject while the subject is within said chamber; and performing plethysmographic measurement of body composition of the infant subject while in said chamber.

32. The method of claim 31, wherein placing the subject in a plethysmographic chamber further comprises:

placing the subject in a tray affixed to the plethysmographic chamber; and sliding the tray into said chamber.

33. The method of claim 32, wherein sliding the subject into said chamber further comprises sliding said tray such that said tray makes contact with a load cell housed in said chamber, and wherein weighing the subject further comprises reading measurements generated by said load cell.

* * * * *